(12) United States Patent
O'Rear et al.

(10) Patent No.: US 6,713,657 B2
(45) Date of Patent: Mar. 30, 2004

(54) CONDENSATION OF OLEFINS IN FISCHER TROPSCH TAIL GAS

(75) Inventors: Dennis J. O'Rear, Petaluma, CA (US); Stephen J. Miller, San Francisco, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 0 days.

(21) Appl. No.: 10/115,129

(22) Filed: Apr. 4, 2002

(65) Prior Publication Data

US 2003/0191198 A1 Oct. 9, 2003

(51) Int. Cl.[7] ............... C07C 1/00; C07C 2/02; C07C 27/00
(52) U.S. Cl. ............ 585/329; 585/502; 585/533; 518/700; 518/702; 518/704; 518/705
(58) Field of Search .................. 518/700, 702, 518/704, 705; 585/329, 502, 533

(56) References Cited

U.S. PATENT DOCUMENTS

| | | |
|---|---|---|
| 4,049,741 A | 9/1977 | Kuo et al. |
| 4,133,841 A | 1/1979 | Cosyns et al. |
| 4,417,086 A | 11/1983 | Miller |
| 4,417,087 A | 11/1983 | Miller |
| 4,423,268 A | 12/1983 | Miller |
| 4,423,269 A | 12/1983 | Miller |
| 4,520,215 A | 5/1985 | Owen et al. |
| 4,699,631 A | 10/1987 | Marion |
| 4,831,203 A | 5/1989 | Owen et al. |
| 4,831,205 A | 5/1989 | Krambeck et al. |
| 4,891,457 A | 1/1990 | Owen et al. |
| 4,966,680 A | 10/1990 | Avidan et al. |
| 4,973,790 A | * 11/1990 | Beech et al. ............ 585/533 |
| 5,009,851 A | 4/1991 | Avidan et al. |
| 5,009,852 A | 4/1991 | Kita et al. |
| 5,034,565 A | 7/1991 | Harandi et al. |
| 5,637,259 A | 6/1997 | Galuszka et al. |
| 5,755,841 A | 5/1998 | Boucot et al. |
| 5,882,614 A | 3/1999 | Taylor, Jr. et al. |
| 5,929,126 A | 7/1999 | Koveal et al. |
| 6,063,349 A | 5/2000 | Koveal, Jr. et al. |

OTHER PUBLICATIONS

Yong et al, Scale–up for Fischer–Tropsch synthesis over iron–manganese catalyst, Annual International Coal Conference (2001, 18th, 2475–2483.*

International Search Report issued in PCT/US03/08758, Sep. 5, 2003.

* cited by examiner

Primary Examiner—J. Parsa
(74) Attorney, Agent, or Firm—Burns, Doane, Swecker & Mathis, L.L.P.

(57) ABSTRACT

Light olefins including LPG contained in unreacted tail gas from a Fischer-Tropsch process are catalytically condensed using an acidic oligomerization/aromatization catalyst to form higher molecular weight $C_5+$ products. Thus, $C_3$–$C_4$ olefins are readily separated from the tail gas and upgraded to more valuable products. In one embodiment, the condensation is conducted on a mixed gas stream of fresh synthesis gas and tail gas from a Fischer-Tropsch process. In another embodiment, the condensation is conducted on a syngas feed to a Fischer-Tropsch reactor and removes a significant portion of catalytically poisonous nitrogen compounds.

25 Claims, 4 Drawing Sheets

CONDENSATION OF OLEFINS IN FISCHER TROPSCH TAIL GAS

BACKGROUND OF THE INVENTION

1. Field of the Invention

This invention relates in general to the Fischer-Tropsch synthesis of hydrocarbons from synthesis gas and more particularly to a process of catalytically converting olefins and light hydrocarbons in Fischer-Tropsch tail gas to more desirable products.

2. Description of Related Art

The Fischer-Tropsch synthesis for the production of hydrocarbons is now well known and described in the technical and patent literature. In this synthesis, a gas composed primarily of CO and $H_2$ (commonly referred to as synthesis gas or syngas) is reacted under catalytic conditions to yield a wide variety of gaseous, liquid and solid hydrocarbonaceous products. Significant amounts of light hydrocarbons ($C_3$ and $C_4$) are produced along with the more valuable $C_5+$ hydrocarbons. These light hydrocarbons are recovered, purified and sold as Liquefied Petroleum Gas (LPG). However, LPG is of lower value than the $C_5+$ products. Also, there are significant costs associated with liquefying and transporting LPG.

To provide a stable operation, the Fischer-Tropsch synthesis normally operates under reaction conditions which only partially convert the synthesis gas. Part of the unreacted synthesis gas (commonly known as tail gas) is recycled to the Fischer-Tropsch reactor. Another part of the unreacted synthesis gas is recycled to the synthesis gas generator where $CO_2$ contained in the unreacted synthesis gas is used to achieve the desired $H_2/CO$ stoichiometry in the synthesis gas. Still another part of the unreacted synthesis gas is used as fuel gas or simply flared.

The tail gas contains LPG and other light hydrocarbons mixed with unconverted synthesis gas and byproducts such as $CO_2$ and water. Recovery of LPG and light hydrocarbons fractions from this stream is difficult because they are relatively dilute (less than about 10 wt. %). An example of the complexity of recovering light hydrocarbon fractions from a Fischer-Tropsch effluent is described in U.S. Pat. No. 4,049,741. Recovery often requires the use of expensive cryogenic techniques. The LPG and light hydrocarbons from the Fischer-Tropsch process are fairly olefinic, i.e., greater than about 50% each of $C_3$ and $C_4$ olefins with typical olefin concentrations of the $C_3$ fraction being 75% and the $C_4$ fraction being 70%. When the tail gas containing olefinic LPG and light hydrocarbons is recycled to the Fischer-Tropsch reactor, a modest amount of these materials is incorporated into the growing hydrocarbon chain but the majority of the light olefins are saturated to form paraffins which consumes valuable hydrogen. When the olefinic LPG and light olefins are recycled to the synthesis gas reactor, they can contribute to coking. Olefins and $C_3+$ hydrocarbons in particular are associated with coke formation.

In addition to the aforementioned problems associated with the recovery of LPG and light hydrocarbons from tail gas, there are additional problems associated with the Fischer-Tropsch synthesis. Traces of catalytically poisonous nitrogen compounds are formed in the syngas generation step. These catalytically poisonous nitrogen compounds include nitrites, most commonly HCN. Ammonia is another catalytically poisonous nitrogen compound present in synthesis gas. Molecular nitrogen is also present but it is not a catalyst poison. The formation of catalytically poisonous nitrogen compounds during syngas generation is described in U.S. Pat. Nos. 6,063,349 and 5,929,126. The nitrogen compounds deactivate the Fischer-Tropsch catalysts which then require that more catalyst and larger reactor volumes be used than would otherwise be necessary. In addition to deactivating the catalyst, the nitrogen compounds are incorporated into the products of the reaction, thus making it more difficult to upgrade the products into more salable products. While molecular nitrogen is itself not a poison, Fischer Tropsch synthesis certain conditions, small portions of the molecular nitrogen can be converted to ammonia, which is a catalyst poison. Thus, removal of catalytically poisonous nitrogen compounds from both gas feeds to the Fischer-Tropsch and gas product streams (which are recycled) must be considered.

From an operational and economic standpoint, a more economical technique to recover at least a portion of the LPG and olefinic light hydrocarbons from the unreacted synthesis gas from the Fischer-Tropsch unit and convert them into more valuable products would be highly desirable. Improvements in the conventional recovery techniques using cryogenic separation would be highly desirable. An economical technique to remove at least a portion of catalytically poisonous nitrogen compounds from synthesis gas prior to entry of the syngas into the Fischer-Tropsch unit likewise would be a desirable feature.

It is an object of the invention to provide an improved process for recovering LPG and light hydrocarbons from Fischer-Tropsch tail gas.

It is another object of the invention to develop a procedure to nitrogen-containing catalyst poisons from synthesis gas prior to entry into Fischer-Tropsch reactors.

These and other objects of the present invention will become apparent to the skilled artisan upon a review of the following description, the claims appended thereto, and the figures of the drawing.

SUMMARY OF THE INVENTION

Light olefins including propylene and butenes in the tail gas from a Fischer-Tropsch process are catalytically condensed (oligomerized and/or aromatized) to form higher molecular weight products including naphtha-boiling range olefins, aromatics and combinations thereof. The condensation is an oligomerization/ aromatization reaction using an acidic catalyst. Due to their higher molecular weight, the products of the condensation are easier to recover from the tail gas. The products of the condensation are separated into a $C_5+$ product stream and unreacted syngas mixed with $CO_2$. At least part of the unreacted syngas is recycled to the Fischer-Tropsch reactor and/or the syngas generator. In this way, the LPG fraction is upgraded to provide more valuable $C_5+$ products.

In one embodiment of the invention, the oligomerization/ aromatization condensation can be conducted on the original synthesis gas feed to the Fischer-Tropsch reactor. In this manner, a significant portion of the catalytically poisonous nitrogen compounds are removed. The poisonous compounds may accumulate on the catalyst that converts the olefins but the catalyst can be regenerated easily by stripping with hot gases or by burning in air.

By virtue of the techniques of the invention, LPG and other light hydrocarbons are more readily separated from the tail gas fraction of a Fischer-Tropsch synthesis while being simultaneously converted to more valuable $C_5+$ products. Additionally, the present invention offers the advantage of removing at least a portion of catalytically poisonous nitrogen compounds present in a syngas feed to a Fischer-Tropsch reactor.

DETAILED DESCRIPTION OF PREFERRED EMBODIMENTS

The process of the invention can be readily integrated in an existing Fischer-Tropsch facility that may include syngas generators, Fischer-Tropsch reactors, separators, solvent and/or catalytic dewaxers, hydrocrackers, reformers and other conventional equipment. The process would normally include at least a syngas generator, at least one Fischer-Tropsch reactor, an oligomerization/aromatization reactor and various recycling means.

The syngas used in the present process can be generated using any of the methods well-known and documented in the art. Generally, the syngas is produced by reacting a gaseous oxidant (oxygen, steam, air, enriched air, $CO_2$ and combinations thereof) with a mixture of low molecular weight hydrocarbon gases including natural gas (primarily $CH_4$). It can also be formed by a reaction of gaseous oxidants with coal, shale, petroleum, etc. Known procedures include partial oxidation with or without catalyst, catalytic steam reforming, and combinations thereof, using fixed or fluid catalyst beds. Suitable syngas generating processes are described in U.S. Pat. Nos. 5,755,841; 5,882,614; 5,637,259; and 4,699,631.

The $CO/H_2$ mixture generated in the syngas reactor is then cycled to a Fischer-Tropsch reactor. As indicated earlier, the Fischer-Tropsch synthesis is well-known and widely documented in patent and technical literature. The synthesis converts syngas into a wide variety of hydrocarbonaceous products by contact with a Fischer-Tropsch catalyst under suitable temperatures and pressures. The reaction is typically conducted at temperatures ranging from about 300°–700° F., preferably about 400°–550° F., pressures ranging from about 10 to 500 psia, preferably about 30 to 300 psia, and catalyst space velocities ranging from about 100 to 10,000 cc/g/hr., preferably about 300 to 3,000 cc/g/hr. The reaction can be conducted in a variety of reactors such as fixed bed reactors containing one or more catalyst beds, slurry reactors, fluidized bed reactors, or a combination of different type reactors. The products may range from $C_1$ to $C_{200}+$ hydrocarbons with a majority in the range of $C_5$–$C_{100}+$.

Products from the Fischer-Tropsch reactor are cycled to a separation zone. Hydrocarbons including $C_5+$ liquids are separated and forwarded to processing areas for conversion into fuels, lubricants, etc. Tail gas recovered from the separation zone contains unreacted syngas (i.e., CO, $H_2$), $CO_2$, and light hydrocarbons including $C_2$–$C_4$ olefins. A portion of the tail gas is recycled to the syngas generator and/or the Fischer-Tropsch reactor. A portion of the tail gas may be drawn off and used as fuel. An important feature of the present invention involves forwarding a significant portion of the tail gas to a reaction zone where it is contacted with an acidic oligomerization/aromatization catalyst, preferably a zeolite.

The oligomerization/aromatization reactor can operate within a wide range of temperatures, pressures and feed rates. Depending on the process conditions and the nature of the catalyst, the product from the oligomerization/aromatization reactor can be olefinic or aromatic. Lower temperature operation favors an olefinic product and higher temperature favors the production of aromatics.

The oligomerization/aromatization reactor and catalyst which may be used in the present invention are described in U.S. Pat. Nos. 5,034,565, 4,966,680, 4,831,205, and 4,831,203, the disclosures of which are incorporated herein in their entirety. In the FCC process described in these patents, the olefin concentration is higher, and there is little or no hydrogen, carbon monoxide, or carbon dioxide present. Olefin oligomerization/aromatization is favored by high pressures, and in the process of the patents, the gas stream is compressed. In the present invention, the olefin stream is more dilute, but compression is avoided because the gas stream is already under moderate pressure (250–500 psig) when it exits the Fischer-Tropsch unit. Also, the oligomerization/aromatization reactor should be operated at above atmospheric pressure, but preferably not in excess of the pressure of the Fischer-Tropsch unit. For maximum olefin oligomerization, the pressure should be as high as possible, and the olefin partial pressure should be at least about 50 kPa. Propylene and butenes are typical olefins in the tail gas. In this invention, the conversion of propylene and butenes by oligomerization and/or aromatization should be at least 25%, preferably at least 40% and most preferably at least 60%. The concentration of propylene and butenes in the feed to the oligomerization/aromatization reactor should be at least 1 wt %, preferably at least 2 wt %, and most preferably at least 5 wt %. The acidic zeolite catalyst used in the oligomerization/aromatization reaction preferably has a $SiO_2/Al_2O_3$ molar ratio of 20:1 to 200:1 and most preferably a silica/alumina molar ratio of about 25:1 to 70:1. The preferred zeolite is ZSM-5. Preferably, the zeolite is bound in an oxide support such as alumina, silica or titania, with alumina being the preferred binder. Preferably, the oligomerization/aromatization reactor is a fluidized bed unit which permits a gradual removal of catalyst with external regeneration and replacement.

Suitable oligomerization/aromatization catalysts and reactors are also described in U.S. Pat. Nos. 4,417,086, 4,417,087, 4,423,268, and 4,423,269, the disclosures of which are incorporated herein in their entirety. Catalysts include ZSM-5 having a silica/alumina ratio greater than 200. A lower ratio is not required for oligomerization, but would be preferred where aromatics were the desired product. While higher pressures favors oligomerization, substantial formation of $C_3$ and $C_4$ dimers and trimers can occur even at total pressures in the 0–100 psig range. Pressures higher than this would be preferred where higher oligomers are sought, e.g. for diesel. Typical GHSV is about 500–2000.

The tail gas feedstock containing lower olefins is contacted with catalyst in an oligomerization/aromatization zone to produce a product having a higher number average molecular weight than the feedstock. Preferably, the product from the oligomerization/aromatization zone has a number average molecular weight at least 10% higher than the feedstock, more preferably at least 20% higher than the feedstock.

Catalysts for oligomerization/aromatization can be virtually any acidic material including zeolites, clays, resins, $BF_3$ complexes, HF, $H_2SO_4$, $AlCl_3$, ionic liquids (preferably acidic ionic liquids), superacids, etc. Preferably, the catalyst includes an inorganic oxide support, more preferably a Group VIII metal on an inorganic oxide support, most preferably a Group VIII metal on a zeolite support. Zeolites are preferred because of their resistance to fouling and ease of regeneration. In one embodiment, the oligomerization catalyst is nickel on ZSM-5. Suitable oligomerization catalysts are disclosed, for example, in U.S. Pat. No. 5,009,851, the entire disclosure of which is incorporated herein by reference. In an alternative embodiment, the oligomerization catalyst comprises an ionic liquid, preferably an acidic ionic liquid.

Conversion of lower olefins, especially ethene, propene and butenes, over HZSM-5 is effective at moderately elevated temperatures and pressures. The conversion products are sought as liquid fuels, especially the $C_5+$ hydrocarbons. Product distribution for liquid hydrocarbons can be varied by controlling process conditions, such as temperature, pressure and space velocity. Gasoline (e.g., $C_5-C_9$) is readily formed at elevated temperature (e.g., up to about 950 F.) and moderate pressure from ambient to about 5500 Kpa (800 psig), preferably about 250 to 2900 Kpa (15–400 psig). Under appropriate conditions of catalyst activity, reaction temperature and space velocity, predominantly olefic gasoline can be produced in good yield and may be recovered as a product.

In one embodiment, the oligomerization/aromatization zone is located in a fluid-bed reactor. In fluid-bed operation, reaction temperature is carefully controlled to maintain a temperature in the normal operating range of about 500° F. to 950° F., preferably at an average reactor temperature of about 600° F. to 750° F. Pressures are typically maintained at up to about 800 psig. Fluid-bed operation further permits the catalyst to be frequently regenerated in order to remove any contaminants, and particularly nitrogen compounds, which may have been adsorbed as a catalyst poison. An oligomerization process using fluid-bed operation is disclosed, for example, in previously mentioned U.S. Pat. No. 5,009,852.

In a separate embodiment, the oligomerization/aromatization zone is located within a catalytic distillation unit used to produce the product and separate the product into a light byproduct fraction and a heavy product fraction. In this embodiment, the olefinic feedstock can also be contacted with the catalyst in a fixed bed prior to the catalytic distillation unit. Preferably, at least a portion of a light byproduct fraction is recycled either to the catalytic distillation unit or to the fixed bed or to both the catalytic distillation unit and the fixed bed. The product from the oligomerization/aromatization zone is separated into a light byproduct fraction for passing to the Fischer-Tropsch hydrocarbon synthesis, and a $C_5+$ liquid fraction. Suitable conditions for an oligomerization/aromatization reaction in a fixed bed reactor or catalytic distillation unit may include a reaction temperature between ambient temperature and about 750° F., from about 0.1 to 3 LHSV, and a pressure from about 0 to 500 psig.

Figure 1:
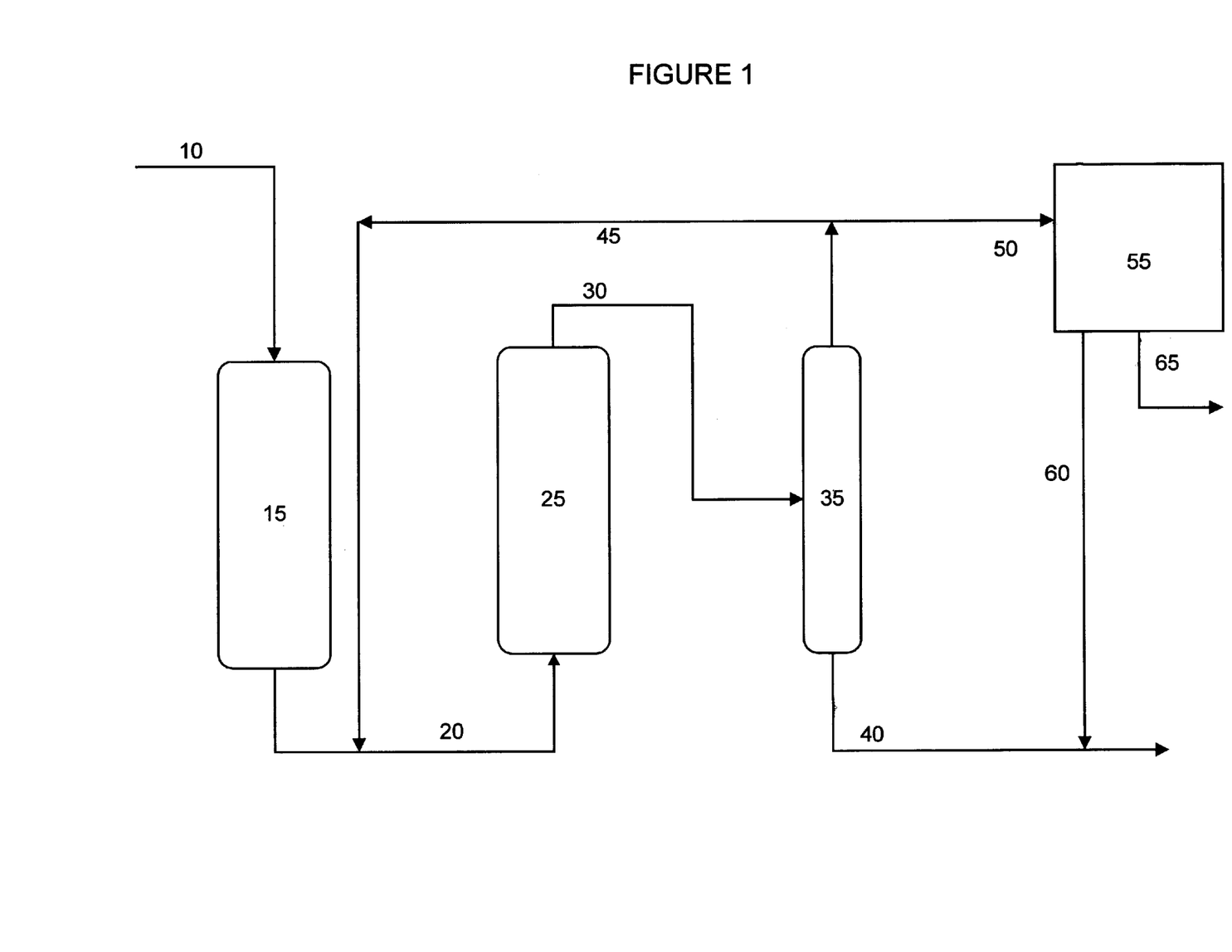
FIG. 1 is a schematic flow diagram of one embodiment of the invention.
Figure 3:
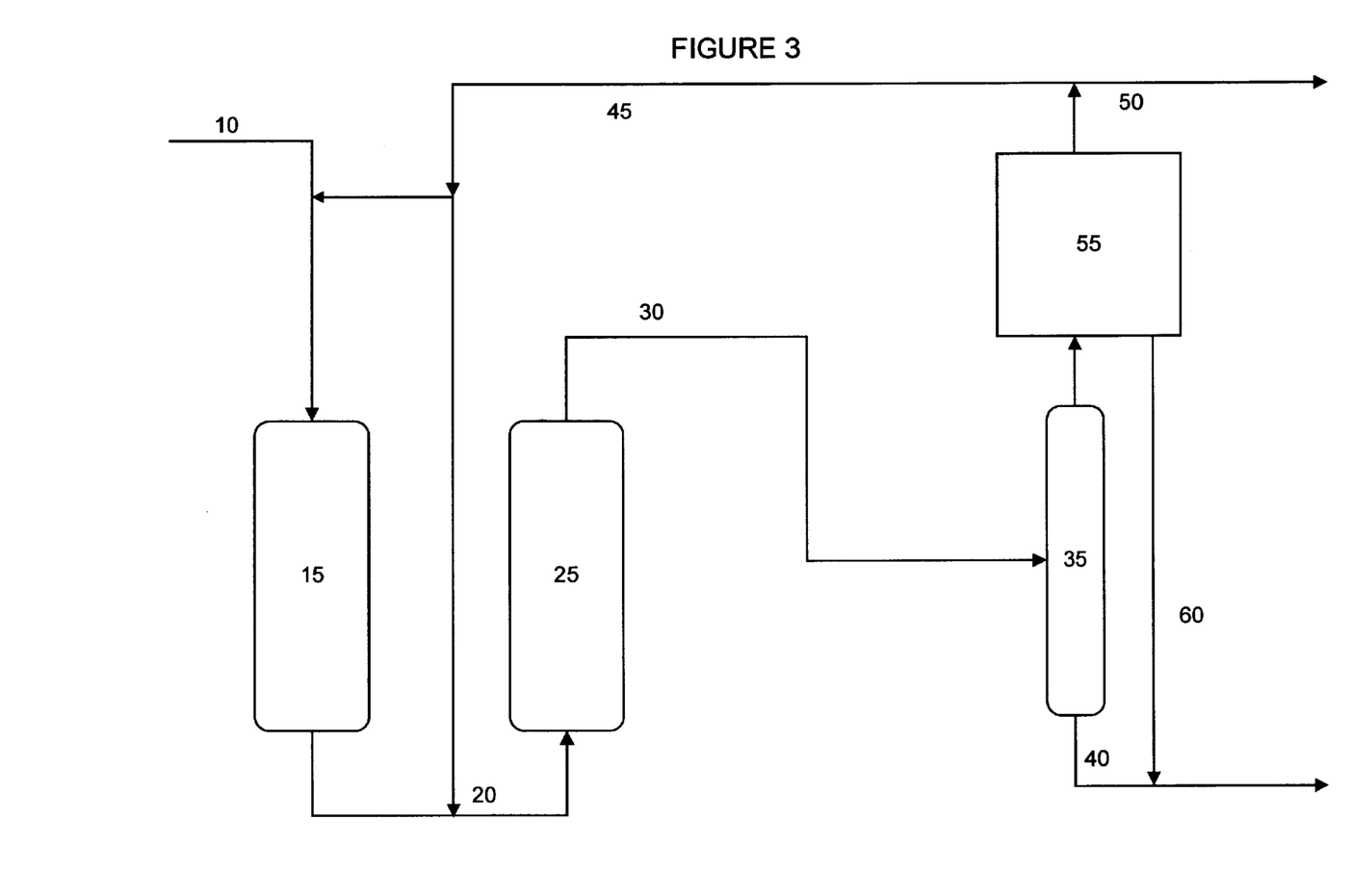
FIG. 3 is a schematic flow diagram of a third embodiment of the invention.

FIGS. 1 and 3 show the recovery of LPG and light hydrocarbons from unreacted synthesis gas from a Fischer-Tropsch unit. In FIG. 1, the light hydrocarbons are recovered from that portion of the tail gas intended to be used as fuel gas. In FIG. 3 the light hydrocarbons are recovered from the tail gas. This reduces the amount of $C_2+$ hydrocarbons going both to fuel and recycled to the syngas generator. Specifically as show in FIG. 3, a synthetic gas-generating mixture comprising methane, oxygen and water is forwarded through conduit 10 to a conventional syngas generator 15. The effluent from the generator 15 composed mainly of CO, $H_2$ and $CO_2$ with trace amounts of HCN and/or $NH_3$ is forwarded through conduit 20 to a Fischer-Tropsch reactor 25 where synthesis occurs to produce a range of hydrocarbonaceous products. Effluent from reactor 25 is forwarded via conduit 30 to a separation zone 35. Hydrocarbon products including $C_5+$ liquids are recovered from separation zone 35 via conduit 40. Tail gas recovered from zone 35 is composed mainly of $C_2-C_4$ hydrocarbons, CO, $H_2$ and $CO_2$. A portion of the tail gas may be recycled via conduit 45 to conduit 10 where it is added to the syngas-generating feed. Alternatively, some or all of this portion of the tail gas may be recycled to conduit 20 to be mixed with the feed to the Fischer-Tropsch reactor 25. At least part of the tail gas recovered from separation zone 35 is forwarded via conduit 50 to an oligomerization/aromatization reactor 55 containing a zeolite catalyst. This catalyst also removes at least a portion of any catalytically poisonous nitrogen compounds exiting from the Fischer-Tropsch reactor that are present in the feed to reactor 55. The $C_5+$ products from reactor 55 are forwarded via conduit 60 to conduit 40 where they are mixed with the $C_5+$ products from separation zone 35 and sent to a recovery and processing facility. Exit gases recovered from reactor 55 are composed mainly of excess CO, $H_2$ and $CO_2$. They are forwarded via conduit 65 for use as fuel.

In the alternate process shown in FIG. 1, reactor 55 is used to process fuel gas to convert light olefins to $C_5+$ products. These products are forwarded via conduit 60 to be mixed with the hydrocarbon products in conduit 40. Excess gas not converted in reactor 55 is forwarded via conduit 65 for use as fuel gas.

Figure 2:
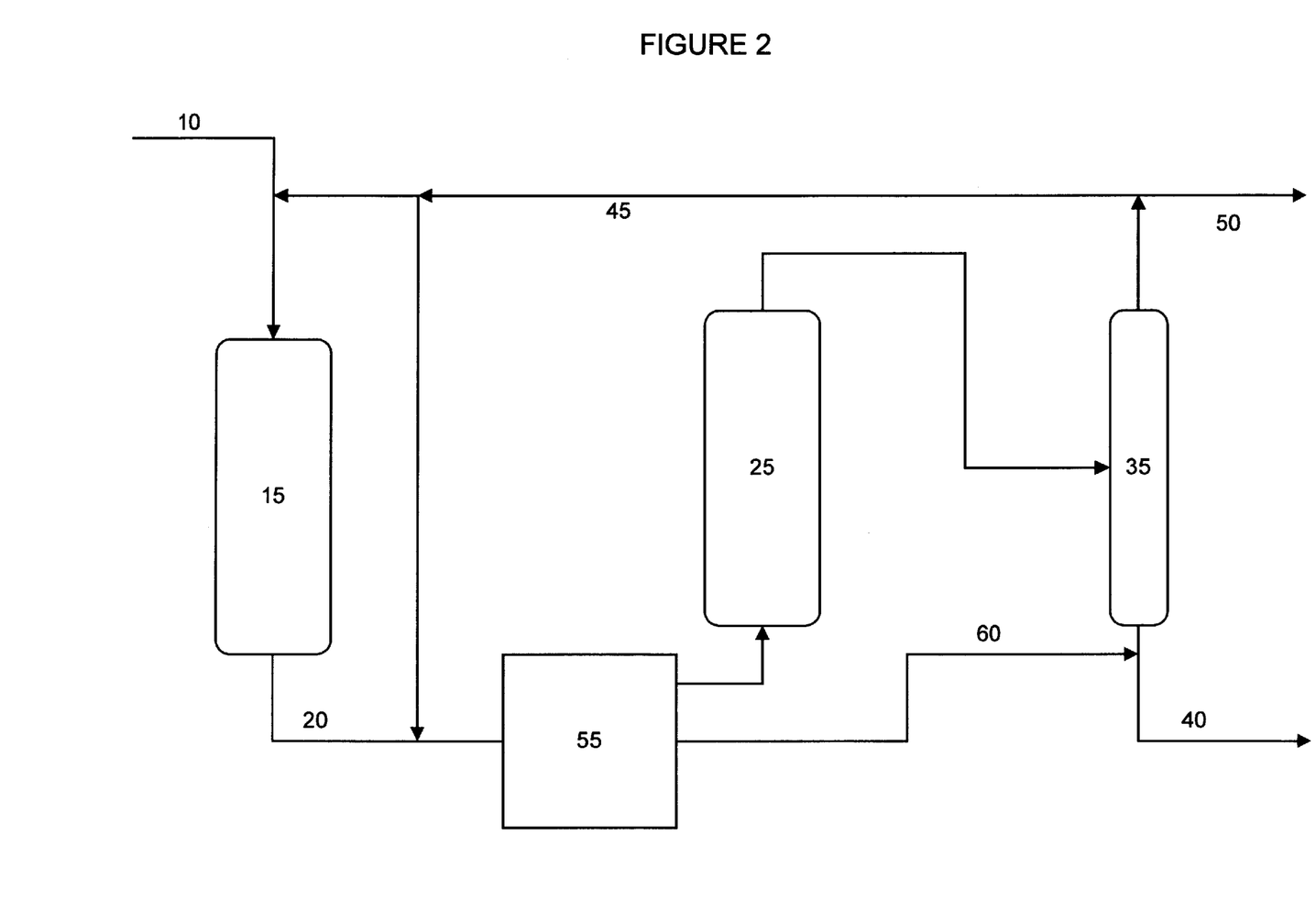
FIG. 2 is a schematic flow diagram of a second embodiment of the invention.

FIG. 2 shows another embodiment for recovery of LPG and light hydrocarbons from unreacted synthesis gas from a Fischer-Tropsch unit. This likewise reduces the amount of $C_2+$ hydrocarbons going both to fuel and recycled to the syngas generator. It also removes catalytically poisonous nitrogen compounds from the synthesis gas generator. A syngas-generating mixture is circulated via conduit 10 to a syngas generator 15. The product from generator 15 is cycled via conduit 20 to an oligomerization/aromatization reaction and separation zone 55. The LPG and poisonous nitrogen compound-depleted syngas product recovered from zone 55 is forwarded to Fischer-Tropsch reactor 25. Fischer-Tropsch reaction product is forwarded to separator 35. Hydrocarbon products including $C_5+$ liquids are recovered from separator 35, admixed with $C_5+$ liquids recovered from reactor 55 and forwarded via conduit 40 to processing and recovery. A portion of tail gas recovered from separator 35 may be recycled via conduit 45 to conduit 10 to be admixed with the feed to syngas generator 15. Preferably, at least a portion of the tail gas in conduit 45 is recycled to conduit 20 where it is admixed with the syngas feed to oligomerization/aromatization reactor 55. Excess CO, $CO_2$ and $H_2$ recovered from separation zone 35 may be used as fuel.

In the embodiment shown in FIG. 2, the oligomerization/aromatization reactor operates on the syngas stream entering the Fischer-Tropsch unit. This gas stream may be a mixture of recycled Fischer-Tropsch tail gas with fresh synthesis gas, the latter being produced in a conventional syngas generator. The fresh synthesis gas normally contains small amounts of catalytically poisonous nitrogen compounds, a portion of which (at least 30% by wt., preferably at least 60% by wt. and most preferably at least 90% by wt.) are removed in the oligomerization/aromatization reactor. This process is most useful when the content of poisonous nitrogen compounds in the feed to the oligomerization/aromatization unit is at least 1 ppm by weight, preferably at least 2 ppm and most preferably at least 5 ppm. These nitrogen compounds contribute to poisoning of the oligomerization/aromatization catalyst, but the catalyst can be regenerated easily by stripping with hot gases (such as hydrogen, nitrogen, or steam) or by burning with air. Some of the catalytically poisonous nitrogen compounds may be present in the heavier products from the oligomerization/ aromatization reactor, but these will by-pass the Fischer-Tropsch reactor, and if needed, can be removed in the Fischer-Tropsch product upgrading facility. The process can be run either with a fixed or fluidized bed of catalyst. By running at milder conditions, which favor oligomerization versus aromatization, catalyst life is extended by minimizing coking. Furthermore, most of the carbonaceous deposits formed on the catalyst at lower temperatures (typically 200°–350° C.) can be stripped off with hot gas, whereas the carbon deposited at higher temperature (above 450° C.) would most likely need to be burned off. The acidic catalyst which converts the LPG does not have components which convert the CO in the syngas. Thus, CO conversion is typically less than 10%, and most typically below 1%.

Figure 4:
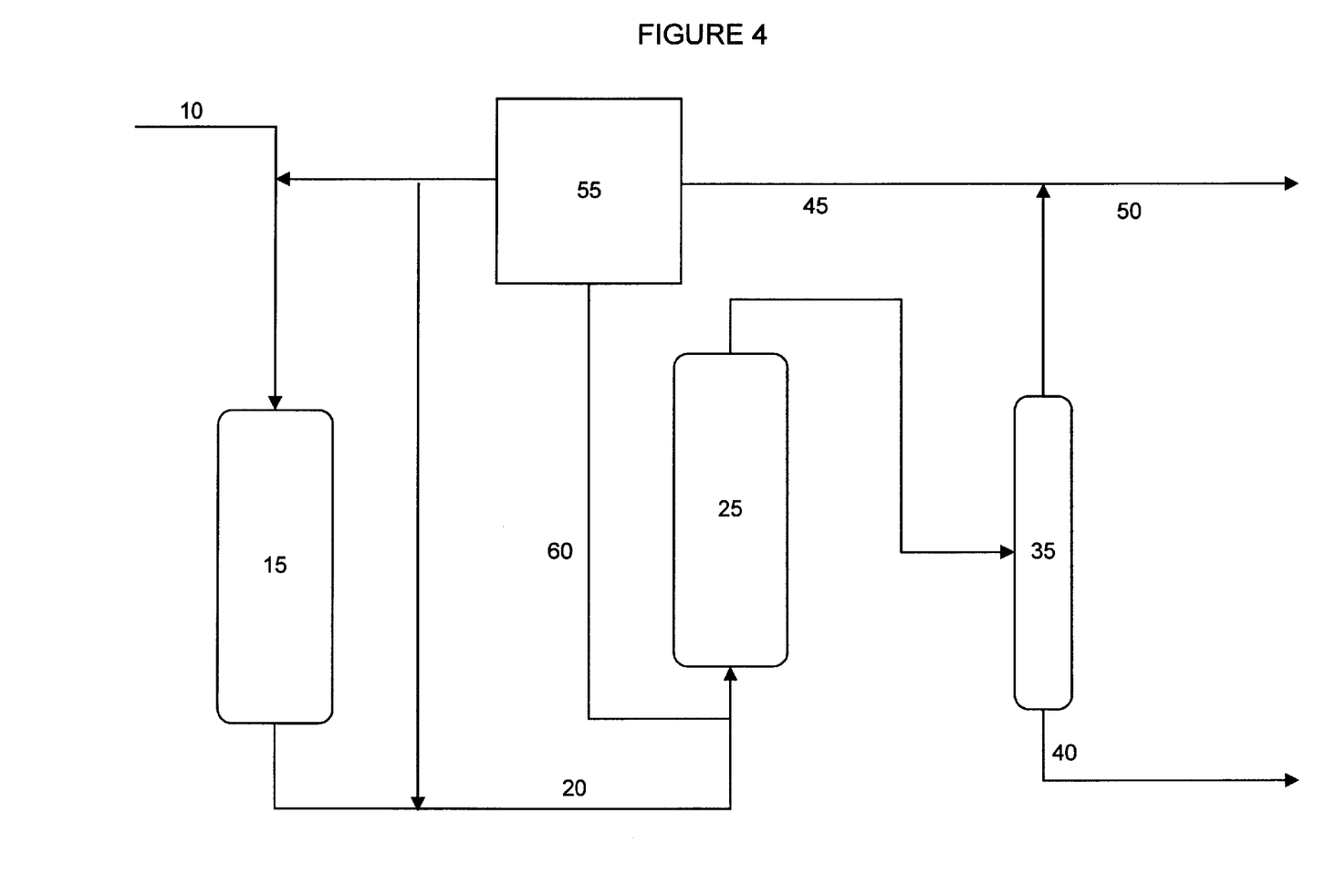
FIG. 4 is a schematic flow diagram of a fourth embodiment of the invention.

In a further embodiment as shown in FIG. 4. The oligomerization/aromatization reactor operates on the exit gas stream from the Fischer-Tropsch unit. Specifically, a portion of the tail gas from Separation zone 35 is circulated via conduit 45 to reactor 55. The $C_5+$ products are recovered and forwarded via conduit 60 to be mixed with the $C_5+$ products from zone 35. Unconverted tail gas containing unreacted syngas is forwarded to conduit 20 for cycling to reactor 25 and/or forwarded to reactor 15 in admixture with fresh syngas. This reduces the amount of catalytically poisonous nitrogen compounds present in the unreacted syngas from the Fischer-Tropsch unit.

After catalyst is withdrawn from the oligomerization/ aromatization reactor for regeneration, it can be used to adsorb the catalytically poisonous nitrogen compounds from the fresh synthesis gas. This adsorption can be done either before or after the oligomerization/aromatization catalyst is regenerated.

The product from the oligomerization/aromatization reactor obtained from a feed that contains catalytically poisonous nitrogen compounds will also contain some nitrogen compounds. This product can be treated prior to blending with the product from the Fischer-Tropsch reactor. Methods of treatment include adsorption and hydrotreating. Alternatively, the product from the oligomerization/ aromatization reactor can be blended with the product from the Fischer-Tropsch unit: and both treated in a common facility to remove the nitrogen compounds in the product from the oligomerization/aromatization reactor while simultaneously removing olefins and oxygenates from the products of the Fischer-Tropsch reactor.

It should be recognized that the same numerals were used in FIGS. 1–4 to refer to identical equipment.

While the invention has been described with preferred embodiments, it is to be understood that variations and modification may be resorted to as will be apparent to those skilled in the art. Such variations and modifications are to be considered within the purview and the scope of the claims appended hereto.

What is claimed is:

1. A process which comprises reacting syngas gas in a generator, reacting syngas in a Fischer-Tropsch reactor, recovering a product stream containing $C_5+$ hydrocarbons and a tail gas fraction containing $C_2$–$C_4$ olefins from the Fischer-Tropsch reactor, forwarding at least a portion of the tail gas fraction to an oligomerization/aromatization reaction zone containing an acidic catalyst, recovering $C_5+$ hydrocarbon products and unreacted syngas therefrom, recycling at least a portion of the unreacted syngas to the syngas generator.

2. A process according to claim 1, wherein said acidic catalyst is a zeolite.

3. A process according to claim 2, wherein the zeolite is ZSM-5.

4. A process according to claim 1, wherein the tail gas fraction contains at least 1 wt. % propylene and butenes.

5. A process according to claim 4, wherein the tail gas fraction contains at least 5 wt. % propylene and butenes.

6. A process according to claim 4, wherein at least 25 wt. % of the propylene and butenes present in the fraction are oligomerized.

7. A process according to claim 6, wherein at least 60 wt. % of the propylene and butenes present in the fraction are oligomerized.

8. A process which comprises producing syngas in a generator, reacting said syngas in a Fischer-Tropsch reaction zone to produce hydrocarbonaceous products, recovering a tail gas fraction containing $C_2$–$C_4$ olefins from the Fischer-Tropsch reaction zone, treating at least part of the tail gas fraction with an acidic oligomerization/aromatization catalyst, recovering a product stream containing $C_5+$ hydrocarbons and a tail gas fraction, recycling a portion of the treated tail gas fraction to the syngas generator, and recycling a portion of the treated tail gas fraction to the Fischer-Tropsch reaction zone.

9. A process according to claim 8, wherein the acidic catalyst is a zeolite.

10. A process according to claim 9, wherein the zeolite is ZSM-5.

11. A process according to claim 8, wherein the tail gas recovered from the Fischer-Tropsch reaction zone contains at least 1 wt. % propylene and butenes.

12. A process according to claim 11, wherein the said tail gas contains at least 5 wt. % propylene and butenes.

13. A process which comprises reacting a feed mixture comprising $CH_4$, $O_2$ and $H_2O$ in a syngas generator, forwarding the syngas so obtained to an oligomerization/ aromatization zone containing an acidic catalyst to produce a $C_5+$ product and a lighter syngas fraction, forwarding the lighter syngas fraction to a Fischer-Tropsch reaction zone, recovering $C_5+$ products and a tail gas fraction and recycling at least a portion of the tail gas fraction to the said feed mixture.

14. A process according to claim 13, wherein the oligomerization/aromatization catalyst comprises a zeolite.

15. A process according to claim 13, wherein the syngas forwarded to the oligomerization/aromatization zone contains at least 1 ppm nitrogen compounds which are poisonous to Fischer-Tropsch catalysts.

16. A process according to claim 15, wherein the syngas contains at least 5 ppm of said poisonous nitrogen compounds.

17. A process according to claim 15, wherein at least 30 wt. % of said poisonous nitrogen compounds are removed from the syngas in the oligomerization/aromatization zone.

18. A process according to claim 17, wherein at least 60 wt. % of the poisonous nitrogen compounds are removed.

19. A process according to claim 17, wherein at least 90 wt. % of the poisonous nitrogen compounds are removed.

20. A process according to claim 14, wherein the zeolite comprises ZSM-5.

21. A process according to claim 1, wherein the acidic oligomerization/aromatization catalyst contains $SiO_2/Al_2O_3$ in a ratio of about 20:1 to about 200:1.

22. A process according to claim 1, wherein the pressure in said oligomerization/aromatization reaction zone is about 250–500 psig.

23. A process according to claim 1, wherein the partial pressure of said olefins in the oligomerization/aromatization reaction zone is at least about 50 KPa.

24. A process according to claim 1, wherein said reaction zone contains a fluidized bed unit.

25. A process according to claim 1 wherein the temperature in said reaction zone ranges from about 200° C. to about 350° C.

* * * * *

UNITED STATES PATENT AND TRADEMARK OFFICE
CERTIFICATE OF CORRECTION

PATENT NO.    : 6,713,657 B2
DATED         : March 30, 2004
INVENTOR(S)   : Dennis J. O'Rear et al.

It is certified that error appears in the above-identified patent and that said Letters Patent is hereby corrected as shown below:

<u>Column 7, Line 64 to Column 8, Line 6,</u>
Please amend claim 1 as follows:

1.   A process which comprises producing syngas in a generator, reacting syngas in a Fischer-Tropsch reactor, recovering a product stream containing $C_5 +$ hydrocarbons and a tail gas fraction containing $C_2$-$C_4$ olefins from the Fischer-Tropsch reactor, forwarding at least a portion of the tail gas fraction to an oligomerization/aromatization reaction zone containing an acidic catalyst, recovering $C_5 +$ hydrocarbon products and unreacted syngas therefrom, recycling at least a portion of the unreacted syngas to the Fischer-Tropsch reactor, and recycling at least a portion of the unreacted syngas to the syngas generator.

Signed and Sealed this

Twenty-seventh Day of July, 2004

JON W. DUDAS
*Acting Director of the United States Patent and Trademark Office*